United States Patent [19]

Benkő et al.

[11] 4,320,127
[45] Mar. 16, 1982

[54] PYRIDO[3,2-e]-AS-TRIAZINES

[75] Inventors: Pál Benkő; András Messmer; György Hajós; Sándor Bátori; Lujza Petöcz; Iboly Kosóczky; Péter Görög, all of Budapest, Hungary

[73] Assignee: Edyt Gyogyszervegyeszeti Gyar, Budapest, Hungary

[21] Appl. No.: 152,833

[22] Filed: May 23, 1980

[30] Foreign Application Priority Data

May 25, 1979 [HU] Hungary .............................. EE 2664

[51] Int. Cl.³ ...................... A61K 31/53; C07D 471/04
[52] U.S. Cl. ...................................... 424/249; 544/184
[58] Field of Search .......................... 544/184; 424/249

[56] References Cited

U.S. PATENT DOCUMENTS 3,549,631 12/1970 Lewis et al. .......................... 544/184

Primary Examiner—John M. Ford
Attorney, Agent, or Firm—Young & Thompson

[57] ABSTRACT

The invention relates to new pyrido[3,2-e]-as-triazine derivatives of the formula I and pharmaceutically acceptable acid addition salts thereof,

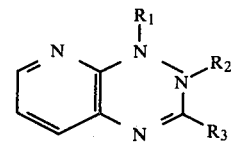

wherein $R_1$ stands for a $C_{1-20}$ alkyl-carbonyl group, halogen-$C_{1-4}$ alkyl-carbonyl, benzoyl, phenyl-$C_{1-4}$ alkyl-carbonyl, or pyridyl-carbonyl group;

$R_2$ is a hydrogen atom or a $C_{1-4}$ alkyl-carbonyl group; or $R_1$ and $R_2$ form together with the adjacent nitrogen atoms a pyrazole-2,4-dione ring which carries a $C_{1-6}$ alkyl substituent in position 3;

$R_3$ is a hydrogen atom, a $C_{1-20}$ alkyl, phenyl, phenyl-$C_{1-3}$ alkyl, furyl or pyridyl group or a phenyl group optionally substituted by one to three $C_{1-4}$ alkoxy-groups.

5 Claims, No Drawings

PYRIDO [3,2-e]-AS-TRIAZINES

This invention relates to new pyrido [3,2-e]-as-triazine derivatives and pharmaceutical compositions containing the same, furthermore to a process for the preparation thereof.

According to a feature of the present invention there are provided compounds of the formula I,

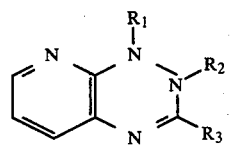

and pharmaceutically acceptable acid addition salts thereof, wherein $R_1$ stands for a $C_{1-20}$ alkyl-carbonyl group, halogen-$C_{1-4}$ alkyl-carbonyl, benzoyl, phenyl-$C_{1-4}$ alkyl-carbonyl, or pyridyl-carbonyl group;

$R_2$ is a hydrogen atom or a $C_{1-4}$ alkyl-carbonyl group; or $R_1$ and $R_2$ form together with the adjacent nitrogen atoms a pyrazole-2,4-dione ring which carries a $C_{1-6}$ alkyl substituent in position 3;

$R_3$ is a hydrogen atom, a $C_{1-20}$ alkyl, phenyl, phenyl-$C_{1-3}$ alkyl, furyl or pyridyl group or a phenyl group optionally substituted by one to three $C_{1-4}$ alkoxy-groups.

Preferred representatives of the new compounds having the formula I are those wherein $R_1$ represents acetyl, propionyl, stearyl, benzoyl, phenylacetyl, phenylpropionyl, chloroacetyl, nicotinoyl or cinnamoyl and $R_2$ represents hydrogen or acetyl, or $R_1$ and $R_2$ form together with the adjacent nitrogen atoms a pyrazole-2,4-dione-3-n-propyl or pyrazole-2,4-dione-3-n-butyl ring and $R_3$ represents n-hexyl, nonyl, n-tridecyl, n-octyl, methyl, benzyl, phenylethyl, phenyl, 4-methoxyphenyl, 3,4,5-trimethoxyphenyl, pyridyl or furyl group, and the pharmaceutically acceptable acid addition salts of these compounds.

Of the new compounds of the formula I the following are particularly preferred:
3-(3',4',5'-trimethoxyphenyl)-1,2-diacetyl-1,2-dihydropyrido[3,2-e]-as-triazine
3-(4'-methoxyphenyl)-1-propionyl-1,2-dihydropyrido[3,2-e]-as-triazine
3-benzyl-1-chloroacetyl-1,2-dihydropyrido[3,2-e]-as-triazine
2-n-butyl-4-methylpyrazolo[1,2-a]pyrido[3,2-e]-as-triazine-1,3-dione
3-n-hexyl-1-propionyl-1,2-dihydropyrido[3,2-e]-as-triazine
3-anisyl-1-propionyl-1,2-dihydropyrido[3,2-e]-as-triazine
3-(3',4',5'-trimethoxyphenyl)-1-propionyl-1,2-dihydropyrido[3,2-e]-as-triazine
2-n-butyl-4-phenylpyrazolo[1,2-a]pyrido[3,2-e]-as-triazine-1,3-dione
3-n-hexyl-1-benzoyl-1,2-dihydropyrido[3,2-e]-as-triazine
3-phenylethyl-1-propionyl-1,2-dihydropyrido[3,2-e]-as-triazine
3-n-hexyl-1-nicotinoyl-1,2-dihydropyrido[3,2-e]-as-triazine and the pharmaceutically acceptable acid addition salts, particularly hydrochlorides, thereof.

The term "alkyl" refers to straight-chained or branched saturated aliphatic hydrocarbyl groups, such as methyl, ethyl, n-propyl, isopropyl, n-butyl etc. The term "alkoxy" refers to groups derived from the alkyl groups mentioned above, such as methoxy, ethoxy, n-propoxy etc. As preferred representatives of the $C_{1-20}$ alkylcarbonyl groups e.g. the acetyl, propionyl and stearyl groups are to be mentioned. An example of the phenyl-($C_{1-4}$ alkyl)-carbonyl groups is the benzyl group, whereas of the $C_{1-4}$ alkoxycarbonyl groups e.g. the methoxycarbonyl and ethoxycarbonyl groups are to be mentioned. The phenyl($C_{2-4}$ alkenyl)-carbonyl group may be preferably a cinnamoyl group. The term "halogen" refers to all the four halogen atoms, i.e. fluorine, chlorine, bromine or iodine.

According to a further feature of the present invention there is provided a process for the preparation of compounds of the formula (I) which comprises reacting a dihydropyrido-as-triazine derivative of the formula (II)

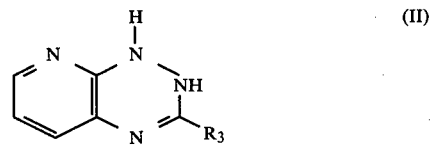

wherein
$R_3$ has the above-specified meaning,
or a salt thereof is reacted with a monofunctional acylating agent of the formula (III),

wherein
$R_1$ has the same meaning as stated above and X is a leaving group,
or with a bifunctional acylating agent of the formula (IV)

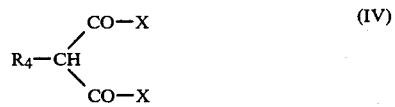

wherein
$R_4$ represents a hydrogen atom or a $C_{1-6}$ alkyl group and X stands for a leaving group,
and, if desired, converting a free base of the formula (I) into its pharmaceutically acceptable acid addition salt, or liberating a base of the formula (I) from its salt.

All acylating agents derived from the appropriate aliphatic, aromatic or heterocyclic carboxylic acids (i.e. the free acids themselves or their halides, anhydrides, esters, etc.) generally applied in the organic chemistry to acylate amines can be used in the process according to the invention.

In most instances the acylating agents can also be applied as reaction medium. In these cases the acylating agent is introduced in excess, and the excess of the acylating agent is removed from the reaction mixture when the reaction terminates. The reaction can also be performed, however, in an inert solvent. In this case no excess of the acrylating agent is required.

When acylating a dihydropyrido-as-triazine derivative of the formula II with an excess of a monofunctional acylating agent of the formula III, the number of the acyl substituents in the end-product depends on the quality of the acylating agent and also on the quality and the volume of the substituent in position 3, further on the stereochemical hindrances.

Suitable solvents are e.g. lower halogenated hydrocarbons, N,N-dialkyl-alkyl-carboxamides, lower nitriles, and aromatic hydrocarbons, dioxane and acetonitrile are mostly optimal as solvents.

The reaction is carried out preferably in the presence of a base, in a wide temperature interval ranging from 10° C. to 250° C.

According to a preferred method of the invention a salt of dihydropyrido-as-triazine is reacted with an equimolar amount of acylating agent, or the dihydropyrido-as-triazine salt is reacted with a great excess of the acylating agent, in the presence of an acid-binding agent.

It is also preferable to start with a free dihydropyrido-as-triazine base of the formula II and to perform the reaction in an inert gas atmosphere.

The leaving group X may preferably be halogen (particularly chlorine), hydroxy, alkoxy or alkanoyloxy.

According to a further method of the process of the present invention acylation is carried out by reacting a dihydropyrido-as-triazine of the formula II or its salt with a bifunctional acylating agent of the general formula IV. In this case special care must be taken of the high purity of the starting dihydropyrido-as-triazine or of its salt, because it results in a higher yield.

Best results can be achieved by adding less than one equivalent of acid-binding agent to the reaction mixture.

As bifunctional acylating agents of the formula IV preferably the respective malic acid dihalides (X=halo) or malic acid esters (X=alkoxy) are used. This reaction provides compounds of the formula I in which $R_1$ and $R_2$ form, together with the adjacent nitrogen atoms, a pyrazole-2,4-dione ring with an alkyl substituent in position 3. This alkyl group corresponds to the $R_4$ group of the acylating agent having the formula (IV). The resulting compounds of the general formula I contain the new pyrazolo (1,2-a)-pyrido[3,2-e]-as-triazine ring system and they are formed in a single step. If a malic acid halide is used as acylating agent, the reaction is performed preferably in the presence of an acid binding agent, such as triethylamine, dimethylamine, etc. It is preferred to use the acid binding agent in an amount not exceeding 75% of the equimolar amount, because in this case the product is obtained under a shorter reaction time in a more easily separable form. If it is necessary, these reactions can also be performed in an inert gas atmosphere.

As follows from their chemical structures, the 1,3-dioxo-derivatives of the new ring system produced by the method described above may also appear in the form of the respective enols. Accordingly, the reaction yields 1-oxo-3-ol, 1-ol-3-oxo or 1,3-diol tautomers or various mixtures thereof. For the sake of clarity these compounds are termed throughout the specification and claims as 1-oxo-3-ol derivatives, formed generally as major components, nevertheless this term covers all of the possible isomers and isomeric mixtures.

The dihydropyrido-as-triazines of the formula II can be prepared in the way described in Hungarian Pat. No. 168,501. The acylating agents of the formulae III and IV are mostly known compounds and can be produced by known methods (e.g. Houben-Weyl: Methoden der präp. Org. Chemie 11/2, 10-14, 16-19, 31-34).

The compounds of the formula I prepared according to this invention are organic bases, so they can form acid addition salts with a number of organic or inorganic acids. In order to prepare acid addition salts of such acids as e.g. sulphuric, phosphoric, hydrochloric, hydrobromic, sulfaminic, citric, maleic, fumaric, tartaric, acetic, benzoic, gluconic, ascorbic acids, the free base and at most two molar equivalents of acid (related to one mole of the free base) are mixed preferably in a suitable inert solvent.

The new compounds of the formula I and therapeutically acceptable acid addition salts thereof possess valuable biological activities. These compounds exert, among others, antiphlogistic, analgesic, narcosis potentiating and tetrabenazine antagonizing effects, so they can be used as active ingredients of pharmaceutical compositions having the above-mentioned activities. A further advantage of the compounds according to the invention is that in suitable form they can be administered in any usual way, e.g. orally, intravenously, intramuscularly or subcutaneously. The pharmaceutical compositions containing the compounds of the formula I or the pharmaceutically acceptable salts thereof can be prepared in solid forms, e.g. in tablets decomposing in the mouth or in the stomach, coated tablets, capsules, pills suppositories, or in liquid forms, e.g. in elixirs solutions, suspensions or syrups. The orally administered compositions containing a dose of about 5-200 mg of ingredient are considered preferable.

The tablets, coated pills, pills and capsules may further contain carriers and/or additives generally applied in the pharmaceutical industry for that purpose, such as binders, e.g. tragacanth, gum arabic, corn starch, gelatin; special binders, e.g. dicalcium phosphate; disintegrants, e.g. corn or potato starch, alginic acid; glidants, e.g. magnesium stearate; sweeteners, e.g. saccharose, lactose, saccharin, or flavours, e.g. mint, sour-cherry jam, gaultheria oil.

Liquid pharmaceutical compositions intended for use by injection, e.g. sterile aqueous solutions or dispersions, may contain solvents or dispersing agents, e.g. water, ethanol, polyols, e.g. glycerine, polyethylene glycols of liquid state, propylene glycol or a suitable mixture thereof or vegetable oils; antibacterial and/or antifungal agents, e.g. chlorobutanol, phenol or sorbic acid. In many cases isotonic solutions are prepared e.g. with the aid of sodium chloride. Therefore any solvent, dispersing, coating, preservative, antibacterial and antifungal agent, etc. is to be understood by the expression "carriers and/or auxiliary materials generally applied in the pharmaceutical industry."

The biological activities of the new compounds according to the invention are illustrated by the following pharmacological tests:

The toxicity of the new compounds according to the invention was determined on mice after oral administration. The $LD_{50}$ values observed are listed in Table 1.

TABLE 1

| Compound No. of Example | $LD_{50}$ mg/kg |
|---|---|
| 18 | 380 |
| 13 | 2000 |
| 1 | 1500 |
| 7 | 2000 |
| 11 | 2000 |
| 6 | 2000 |

TABLE 1-continued

| Compound No. of Example | LD$_{50}$ mg/kg |
|---|---|
| 5 | 750 |
| Meprobamate | 1100 |
| Amitriptyline | 225 |
| Paracetamol | 510 |
| Acetylsalicylic acid | 1500 |

The effect of the compounds on the motility of mice was orally tested in a Dews apparatus, by the method of Borsy et al. (Arch. Int. Pharmacodyn. 124 1-2 (1960). The ED$_{50}$ values and the therapeutical indices are listed in Table 2.

TABLE 2

| Compound No. of Example | ED$_{50}$ mg/kg | Therapeutical index |
|---|---|---|
| 1 | about 200 | 7.5 |
| 7 | over 400 | under 5 |
| 11 | about 200 | about 10 |
| 6 | about 400 | about 5 |
| 5 | about 170 | 4.4 |
| Meprobamate | 270 | 4.1 |

The effect of the compounds exerted on the duration of hexobarbital-narcosis was orally tested on mice by the method of Kaergaard (Arch. Int. Pharmacodyn. 2 170 (1967)). The ED$_{50}$ values and the therapeutical indices are given in Table 3.

TABLE 3

| Compound No. of Example | ED$_{50}$ mg/kg | Therapeutical index |
|---|---|---|
| 18 | 80 | 5 |
| 1 | about 400 | about 5 |
| 7 | over 400 | below 5 |
| 11 | 140 | 14.3 |
| 6 | about 350 | 5.7 |
| 5 | about 170 | 4.4 |
| Meprobamate | 260 | 4.2 |

The tetrabenazine-reserpine antagonistic effect was investigated on mice at oral administration by the method of Brodie et al. (Psychopharmacologia 2, 467-474 (1963)). The ED$_{50}$ values and the therapeutical indices are shown in Table 4.

TABLE 4

| Compound No. of Example | Tetrabenazine antagonism, ED$_{50}$ mg/kg | Therapeutic index | Reserpine antagonism ED$_{50}$ mg/kg | Therapeutic index |
|---|---|---|---|---|
| 18 | 10 | 38 | 30 | 12.7 |
| 1 | 300 | 5 | 300 | 5 |
| 5 | 80 | 9.4 | 170 | 4.4 |
| Amitriptylin | 12 | 18.75 | 65 | 3.46 |

The analgesic effect of the new compounds was determined on mice at oral administration by the acetic acid writhing test. The ED$_{50}$ values and the therapeutical indices are given in Table 5.

TABLE 5

| Compound No. of Example | ED$_{50}$ mg/kg | Therapeutical index |
|---|---|---|
| 18 | about 38 | 10 |
| 13 | over 400 | below 5 |
| 7 | over 400 | below 5 |

TABLE 5-continued

| Compound No. of Example | ED$_{50}$ mg/kg | Therapeutical index |
|---|---|---|
| 11 | about 400 | 5 |
| 6 | 215 | 9.3 |
| 5 | 52 | 14.4 |
| Paracetamol | 180 | 2.8 |

The above-mentioned effects are complemented by antiphlogistic and week anticonvulsive effects. The antiphlogistic (oedema-inhibiting) effect was tested on rats. 0.1 ml of a 1% carrageenin solution were injected into the plantar region of one of the hind paws. The volume of the paw was measured just before and 3 hours after the introduction of oedema-provoking agent by a mercury plethysmometer. The dosages which inhibit the inflammation by 30% (ED$_{30}$; significant effect) are given in Table 6.

TABLE 6

| Compound No. of Example | ED$_{30}$ mg/kg | Therapeutical index |
|---|---|---|
| 18 | about 70 | 5.4 |
| 13 | over 400 | below 5 |
| 1 | 200 | 7.5 |
| 6 | about 155 | 12.9 |
| 5 | 75 | 10 |
| Acetylsalicylic acid | 180 | 8.33 |

The daily oral dose of the compounds of the formula I amounts approximately to about 50–1000 mg. These values are, however, nearly of an informative character and the actually applied dose depends on the circumstances of the given case and the prescriptions of the physician and may lay below or above the said interval.

The invention is illustrated by the following Examples of non-limiting character:

EXAMPLE 1

Preparation of 3-n-hexyl-1-propionyl-1,2-dihydropyrido[3,2-e]-as-triazine hydrochloride A mixture of 12.0 g (0.041 mole) of 3-hexyl-1,2-dihydropyrido[3,2-e]-as-triazine dihydrochloride and 70 ml of propionic anhydride is stirred under argon at 120°–130° C. On cooling the reaction mixture the crystalline product separates within an hour.

Yield: 10.3 g (80%).
M.p.: 147°–148° C.
Analysis: calculated N % = 18.03; found N % = 18.13.
Mol. wt.: 310.

EXAMPLE 2

Preparation of 3-nonyl-1-propionyl-1,2-dihydropyrido[3,2-e]-as-triazine hydrochloride 12.0 g (0.04 mole) of 3-nonyl-1,2-dihydropyrido-[3,2-e]-as-triazine dihydrochloride are treated by the method described in Example 1.

Yield: 9.1 g (71%).
M.p.: 127°–128° C.
Analysis: calculated N % = 15.88; found N % = 15.69.
Mol. wt.: 352.

EXAMPLE 3

Preparation of
3-tridecanyl-1-propionyl-1,2-dihydropyrido-[3,2-e]-as-triazine hydrochloride Starting from 12.0 g (0.034 mole) of 3-tridecanyl-1,2-dihydropyrido[3,2-e]-as-triazine dihydrochloride one proceeds in the way as specified in Example 1.
Yield: 7.2 g (57%).
M.p.: 130°-131° C.
Analysis: calculated N % = 13.70; found N % = 13.48.
Mol. wt.: 409.

EXAMPLE 4

Preparation of
3-benzyl-1-propionyl-1,2-dihydropyrido[3,2e]-as-triazine hydrochloride Starting from 12.0 g (0.04 mole) of 3-benzyl-1,2-dihydropyrido[3,2-e]-as-triazine dihydrochloride one proceeds in the way specified in Example 1.
Yield: 9.3 g (73%).
M.p.: 193°-194° C.
Analysis: calculated N % = 17.68; found N % = 17.53.
Mol. wt.: 316.

EXAMPLE 5

Preparation of
3-anisyl-1-propionyl-1,2-dihydropyrido[3,2-e]-as-triazine hydrochloride Starting from 12.0 g (0.039 mole) of 3-anisyl-1,2-dihydropyrido[3,2-e]-as triazine dihydrochloride one proceeds in the way as specified in Example 1.
Yield: 6.9 g (75%).
M.p.: 226°-227° C.
Analysis: calculated N % = 16.83; found N % = 16.47.
Mol. wt.: 332.

EXAMPLE 6

Preparation of
3-(3',4',5'-trimethoxyphenyl)-1-propionyl-1,2-dihydropyrido[3,2-e]-as-triazine hydrochloride Proceeding by the method described in Example 1 one starts from 12.0 g (0.032 mole) of 3-(3',4',5'-trimethoxyphenyl)-1,2-dihydropyrido-[3,2-e]-as-triazine dihydrochloride.
Yield: 10.8 g (85%).
M.p.: 231°-232° C.
Analysis: calculated N % = 14.22; found N % = 14.67.
Mol. wt.: 393.
Melting point of the base liberated in alkaline medium: 195°-196° C.
Mol. wt.: 357.

EXAMPLE 7

Preparation of
3-phenetyl-1-propionyl-1,2-dihydropyrido-[3,2-e]-as-triazine 4 g (0.012 mole) of 3-phenetyl-1,2-dihydropyrido-[3,2-e]-as-triazine hydrochloride are treated as described in Example 1, and the hydrochloride of the title-compound is obtained with a yield of 85%. The free base is liberated with sodium hydroxide.
Yield: 3.0 g (85%).
M.p.: 157°-158° C.
Analysis: calculated N % = 19.0; found N % = 19.1.
Mol. wt.: 294.

EXAMPLE 8

Preparation of
3-phenyl-1-propionyl-1,2-dihydropyrido[3,2-e]-as-triazine hydrochloride Starting from 5 g (0.02 mole) of 3-phenyl-1,2-dihydropyrido[3,2-e]-as-triazine hydrochloride one proceeds in the way as specified in Example 1.
Yield: 5 g (82%).
M.p.: 257° C.
Analysis: calculated N % = 18.5; found N % = 18.7.
Mol. wt.: 302.

EXAMPLE 9

Preparation of
3-octyl-1-phenylacetyl-1,2-dihydropyrido-as-triazine hydrochloride The desired compound is obtained by reacting 12 g (0.03 mole) of 3-octyl-1,2-dihydropyrido[3,2-e]-as-triazine dihydrochloride with a mixed anhydride of phenylacetic acid and benzoic acid as described in Example 1.
Yield: 7.7 g (64%).
M.p.: 142°-143° C.
Analysis: calculated N % = 13.97; found N % = 13.92.
Mol. wt.: 401.

EXAMPLE 10

Preparation of
3-(3',4',5'-trimethoxyphenyl)-1,2-diacetyl-1,2-dihydropyrido[3,2-e]-as-triazine hydrochloride 12.0 g (0.032 mole) of 3-(3',4',5'-trimethoxyphenyl)-1,2-dihydropyrido[3,2-e]-as-triazine hydrochloride are boiled in 40 ml of glacial acetic acid for a short time. The reaction mixture is cooled and the separated product is filtered off.
Yield: 11.5 g (85%).
M.p.: 240°-241° C.
Analysis: calculated N % = 13.45; found N % = 13.22.
Mol. wt.: 420.
Melting point of the base liberated in alkaline medium: 219°-220° C.
Melting point of its salt formed with citric acid: 199°-200° C.

EXAMPLE 11

Preparation of
3-n-hexyl-1-nicotinoyl-1,2-dihydropyrido-[3,2-e]-as-triazine dihydrochloride 12 g (0.04 mole) of 3-n-hexyl-1,2-dihydropyrido-[3,2-e]-as-triazine dihydrochloride are boiled with an excess of nicotinic chloride. The reaction mixture is cooled and the separated product is filtered off.
Yield: 12.7 g (80%).
M.p.: 197°-198° C.
Analysis: calculated N % = 17.67; found N % = 17.49.
Mol. wt.: 396.

EXAMPLE 12

Preparation of
3-phenethyl-1-phenylpropionyl-1,2-dihydropyrido[3,2-e]-as-triazine hydrochloride 4 g (0.012 mole) of 3-phenethyl-1,2-dihydropyrido-[3,2-e]-as-triazine hydrochloride are reacted with an excess of phenylpropionyl chloride. The reaction mixture is cooled and the separated product is filtered off.
Yield: 3.6 g (74%).

M.p.: 191°–192° C.
Analysis: calculated N % = 13.76; found N % = 13.59.
Mol. wt.: 406.

EXAMPLE 13

Preparation of
2-butyl-4-phenylpyrazolo[1,2-a]pyrido[3,2-e]-as-triazine-1,3-dione 4.0 g (0.014 mole) of phenyl-1,2-dihydropyrido-[3,2-e]-as-triazine dihydrochloride and 4.34 g (0.043 mole) of triethylamine are stirred in 50 ml of dioxane under argon, thereafter 2.6 g (0.014 moles) of butyl-malonyl chloride dissolved in 20 ml of dioxane are added to the thus-obtained orange-coloured suspension within a short time. After stirring at 60°–70° C. for an hour the precipitate is washed to be free from triethylamine.
Yield: 3.4 g (62%).
M.p.: 302°–303° C.
Analysis: calculated N % = 16.75; found N % = 16.39.
Mol. wt.: 334.
Melting point of its salt formed with hydrogen fumarate: 296°–297° C.

EXAMPLE 14

Preparation of
2-butyl-4-phenethyl-pyrazolo[1,2-a]pyrido-[3,2-e]-as-triazine-1,3-dione Starting from 3-phenethyl-1,2-dihydropyrido-[3,2-e]-as-triazine dihydrochloride one proceeds as described in Example 13.
Yield: 2.5 g (53%).
M.p.: 216°–218° C.
Analysis: calculated N % = 15.45; found N % = 15.27.
Mol. wt.: 362.

EXAMPLE 15

Preparation of
2-butyl-4-methylpyrazolo[1,2-a]pyrido[3,2-e]-as-triazine-1,3-dione On starting from 4 g (0.018 mole) of 3-methyl-1,2-dihydropyrido-as-triazine dihydrochloride one proceeds in the way as specified in Example 13.
Yield: 1.9 g (40%).
M.p.: 218° C.
Analysis: calculated N % = 20.57; found N % = 20.36.
Mol. wt.: 272.

EXAMPLE 16

Preparation of
2-propyl-4-phenylpyrazolo[1,2-a]pyrido-[3,2-e]-as-triazine-1,3-dione 4 g (0.014 mole) of 3-phenyl-1,2-dihydropyrido-[3,2-e]-as-triazine are reacted with an equimolar amount of propylmalonic dichloride as described in Example 13.
Yield: 3.2 g (70%).
M.p.: 306°–307° C.
Analysis: calculated N % = 17.49; found N % = 17.22.
Mol. wt.: 320.

EXAMPLE 17

Preparation of
2-propyl-4-(3'-pyridyl)-pyrazolo[1,2-a]-pyrido[3,2-e]-as-triazine-1,3-dione On starting from 9.4 g (0.04 mole) of 3-(3'-pyridyl)-1,2-dihydropyrido[3,2-e]-as-triazine dihydrochloride one proceeds by the method described in Example 16.

Yield: 6.7 g (52%).
M.p.: 214°–215° C.
Analysis: calculated N % = 21.79; found N % = 21.50.
Mol. wt.: 321.
Melting point of its salt formed with maleic acid: 200°–202° C.

EXAMPLE 18

Preparation of
3-hexyl-1-benzoyl-1,2-dihydropyrido[3,2-e]-as-triazine hydrochloride 3 g (0.01 mole) of 3-hexyl-1,2-dihydropyrido-[3,2-e]-as-triazine dihydrochloride are reacted with 2 g (0.02 mole) of triethylamine in 60 ml of anhydrous acetonitrile under argon, thereafter 2.9 g (0.02 mole) of benzoylchloride are added to the reaction mixture which is boiled for an hour. Then the mixture is cooled, poured into water, neutralized and extracted with chloroform. The solvent is evaporated and the residue is reacted with anhydrous hydrochloric ethanol to form a salt.
Yield: 2.4 g (67%).
M.p.: 174°–176° C.
Analysis: calculated N % = 15.61; found N % = 15.26.
Mol. wt.: 358.

EXAMPLE 19

Preparation of
3-hexyl-1-phenylacetyl-1,2-dihydropyrido-[3,2-e]-as-triazine hydrochloride One proceeds as described in Example 18 with the difference that phenylacetyl chloride is used, instead of benzoyl chloride.
Yield: 2.7 g (71%).
M.p.: 205°–206° C.
Analysis: calculated N % = 15.03; found N % = 15.13.
Mol. wt.: 372.

EXAMPLE 20

Preparation of
3-hexyl-1-cinnamoyl-1,2-dihydropyrido[3,2-e]-as-triazine hydrochloride One proceeds as described in Example 18 with the difference that cinnamoyl chloride is used, instead of benzoyl chloride.
Yield: 3.0 g (74%).
M.p.: 227°–228° C.
Analysis: calculated N % = 14.58; found N % = 14.40.
Mol. wt.: 384.

EXAMPLE 21

Preparation of
3hexyl-1-chloroacetyl-1,2-dihydropyrido-[3,2-e]-as-triazine hydrochloride One proceeds as described in Example 18 with the difference that chloroacetyl chloride is used, instead of benzoyl chloride.
Yield: 3 g (85%).
M.p.: 136°–137° C.
Analysis: calculated N % = 16.91; found N % = 16.78.
Mol. wt.: 331.

EXAMPLE 22

Preparation of
3-benzyl-1-stearoyl-1,2-dihydropyrido[3,2-e]-as-triazine hydrochloride 3-Benzyl-1,2-dihydropyrido[3,2-e]-as-triazine and stearyl chloride are reacted in the way specified in Example 18.

Yield: 4.5 g (89%).
M.p.: 167°–168° C.
Analysis: calculated N %=10.63; found N %=10.40.
Mol. wt.: 527.

EXAMPLE 23

Preparation of
3-(2-furyl)-1-propionyl-1,2-dihydropyrido-[3,2-e]-as-triazine hydrochloride 3-(2-furyl)-1,2-dihydropyrido[3,2-e]-as-triazine and propionic anhydride are reacted in the way described in Example 1.

Yield: 10 g (86%).
M.p.: 218°–219° C.
Analysis: calculated N %=19.21; found N %=19.11.
Mol. wt.: 291.

EXAMPLE 24

Preparation of
3-benzyl-1-chloroacetyl-1,2-dihydropyrido-[3,2-e]-as-triazine hydrochloride 3-Benzyl-1,2-dihydropyrido[3,2-e]-as-triazine and chloroacetic chloride are reacted in the way described in Example 18.

Yield: 2.86 g (85%).
M.p.: 223°–224° C.
Anaylsis: calculated N %=16.67; found N %=16.60.
Mol. wt.: 336.

What we claim is:

1. A pyrido[3,2-e]-as-triazine derivative of the formula I or a pharmaceutically acceptable acid addition salt thereof,

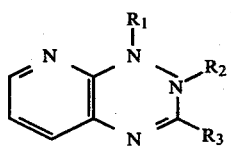

$R_1$ stands for a $C_{1-20}$ alkyl-carbonyl group, halogen-$C_{1-4}$alkyl-carbonyl, benzoyl, phenyl-$C_{1-4}$alkyl-carbonyl, or pyridyl-carbonyl group;

$R_2$ is a hydrogen atom or a $C_{1-4}$ alkyl-carbonyl group; or $R_1$ and $R_2$ form together with the adjacent nitrogen atoms a pyrazole-2,4-dione ring which carries a $C_{1-6}$ alkyl substituent in position 3;

$R_3$ is a hydrogen atom, a $C_{1-20}$ alkyl, phenyl, phenyl-$C_{1-3}$alkyl, furyl or pyridyl group or a phenyl group optionally substituted by one to three $C_{1-4}$ alkoxy-groups.

2. A compound as claimed in claim 1, wherein $R_1$ represents acetyl, propionyl, stearyl, benzoyl, phenylacetyl, phenylpropionyl, chloroacetyl or nicotinoyl, and $R_2$ represents hydrogen or acetyl, or $R_1$ and $R_2$ form together with the adjacent nitrogen atoms a pyrazole-2,4-dione-3-n-propyl or pyrazole-2,4-dione-3-n-butyl ring and $R_3$ represents n-hexyl, n-nonyl, n-tridecyl, n-octyl, methyl, benzyl, phenylethyl, phenyl, 4-methoxyphenyl, 3,4,5-trimethoxyphenyl, pyridyl or furyl group, or a pharmaceutically acceptable acid addition salt thereof.

3. A compound as claimed in claim 1, selected from the group consisting of 3-(3',4',5'-trimethoxyphenyl)-1,2-diacetyl-1,2-dihydropyrido[3,2e]-as-triazine, 3-(4'-methoxyphenyl)-1-propionyl-1,2-dihydropyrido[3,2-e]-as-triazine, 3-benzyl-1-chloroacetyl-1,2-dihydropyrido[3,2-e]-as-triazine, 2-n-butyl-4-methyl-pyrazolo(1,2-a)pyrido[3,2-e]-as-triazine-1,3-dione, 3-n-hexyl-1-propionyl-1,2-dihydropyrido[3,2-e]-as-triazine, 3-anisyl-1-propionyl-1,2-dihydropyrido[3,2-e]-as-triazine, 3-(3',4',5'-trimethoxyphenyl)-1-propionyl-1,2-dihydropyrido[3,2-e]-as-triazine, 2-n-butyl-4-phenyl-pyrazolo[1,2-a]pyrido[3,2-e]-as-triazine-1,3-dione, 3-n-hexyl-1benzoyl-1,2-dihydropyrido[3,2-e]-as-triazine, 3,-phenylethyl-1-propionyl-1,2-dihydropyrido[3,2-e]-as-triazine, 3-n-hexyl-1-nicotinoyl-1,2-dihydropyrido[3,2-e]-as-triazine, or a pharmaceutically acceptable acid addition salt thereof.

4. A compound as claimed in claim 1, selected from the group consisting of 3-n-hexyl-1-propionyl-1,2-dihydropyrido[3,2-e]-as-triazine hydrochloride, 3-anisyl-1-propionyl-1,2-dihydropyrido[3,2-e]-as-triazine hydrochloride, 3-(3',4',5'-trimethoxyphenyl)-1-propionyl-1,2-dihydropyrido[3,2-e]-as-triazine hydrochloride, 3-n-hexyl-1-nicotinoyl-1,2-dihydropyrido[3,2-e]-as-triazine dihydrochloride, 3-hexyl-1-benzoyl-1,2-dihydropyrido[3,2-e]-as-triazine hydrochloride, or a pharmaceutically acceptable acid addition salt thereof.

5. A pharmaceutical composition having sedative and antidepressive effects, containing as active agent a sedative and antidepressive effective amount of a compound of the formula I or a pharmaceutically acceptable acid addition salt thereof, wherein $R_1$, $R_2$ and $R_3$ are as defined in claim 1, together with an appropriate inert, non-toxic, solid or liquid pharmaceutical carrier.

* * * * *